United States Patent [19]

Tsugita et al.

[11] Patent Number: 5,051,369
[45] Date of Patent: Sep. 24, 1991

[54] DETECTION METHOD FOR AMINO ACID DERIVATIVE

[75] Inventors: Akira Tsugita, Kashiwa; Toyoaki Uchida, Tokyo, both of Japan

[73] Assignee: Seiko Instruments Inc., Japan

[21] Appl. No.: 227,184

[22] Filed: Aug. 2, 1988

[51] Int. Cl.$^5$ .................. G01N 21/64; G01N 33/68
[52] U.S. Cl. .................. 436/89; 436/92; 530/345; 530/408
[58] Field of Search .................. 436/89, 92, 172; 530/345, 408

[56] References Cited

U.S. PATENT DOCUMENTS

| | | | |
|---|---|---|---|
| 4,155,714 | 5/1979 | Bonner et al. | 422/109 |
| 4,587,102 | 5/1986 | Nagatomo et al. | 422/56 |
| 4,861,726 | 8/1989 | Stolowitz et al. | 436/89 |
| 4,865,994 | 9/1989 | Tsugita et al. | 436/89 |

FOREIGN PATENT DOCUMENTS 0202894  11/1986  European Pat. Off. .

OTHER PUBLICATIONS

Agr. Biol. Chem., vol. 40, No. 4, 1976, pp. 815–817, K. Muramoto et al., "Analysis of Fluorescein-Thiohydantoin Amino Acids by High Speed Liquid Chromatography".
Analytical Biochemistry, vol. 77, 1977, pp. 569–573, Academic Press, C. L. Zimmerman et al., "Paid Analysis of Amino Acid Phenylthiohydantoins by High-Performance Liquid Chromatography".
Tsugita et al., "Sensitization of Amino Acid Derivatives Obtained from Edman Degradation with Radioactively-Labelled Jodohistamine", *J. Biochem.*, vol. 103, No. 3, pp. 399–401, 1988.

*Primary Examiner*—Robert J. Hill, Jr.
*Attorney, Agent, or Firm*—Bruce L. Adams; Van C. Wilks

[57] ABSTRACT

A method for detecting amino acid derivatives in which 2-anilino-5-thiazolinone derivatives of amino acids are reacted with an amino compound of fluorescein or rhodamine derivative amino compounds to form phenylthiocarbamyl amino acids derivatives. The phenylithiocarbamyl amino acids derivatives are detected with a high level of sensitivity by a fluorescence spectrophotometer.

1 Claim, 3 Drawing Sheets

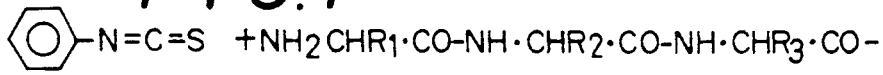
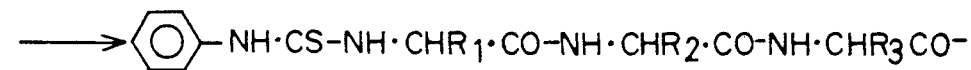
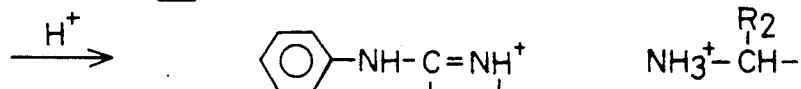
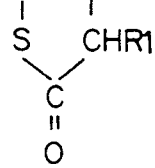
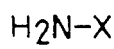
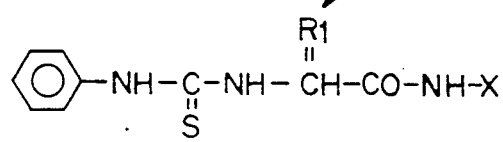
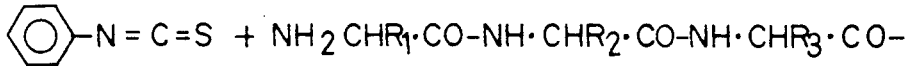
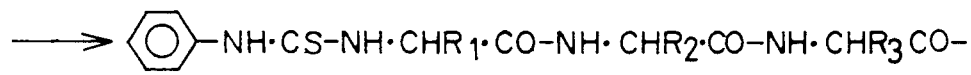
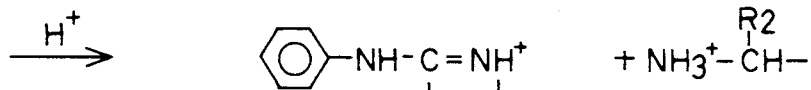
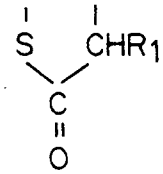
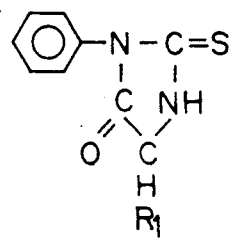

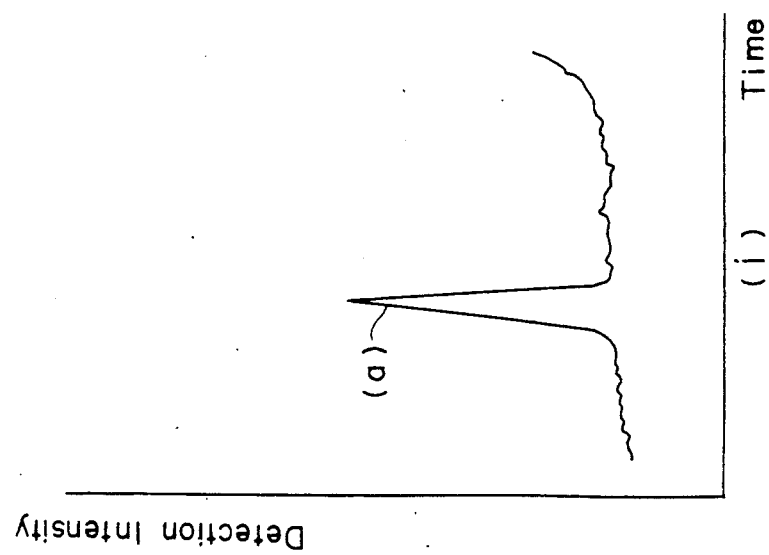
FIG. 4
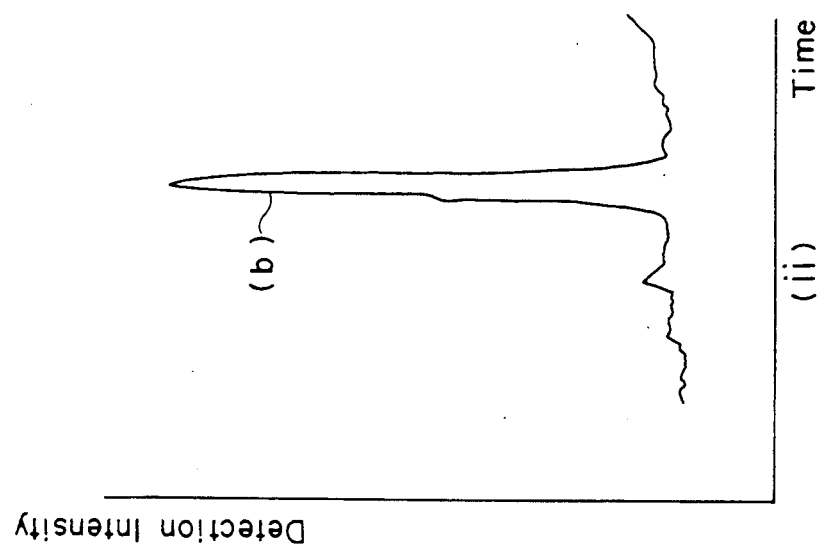
FIG. 3 (ii)
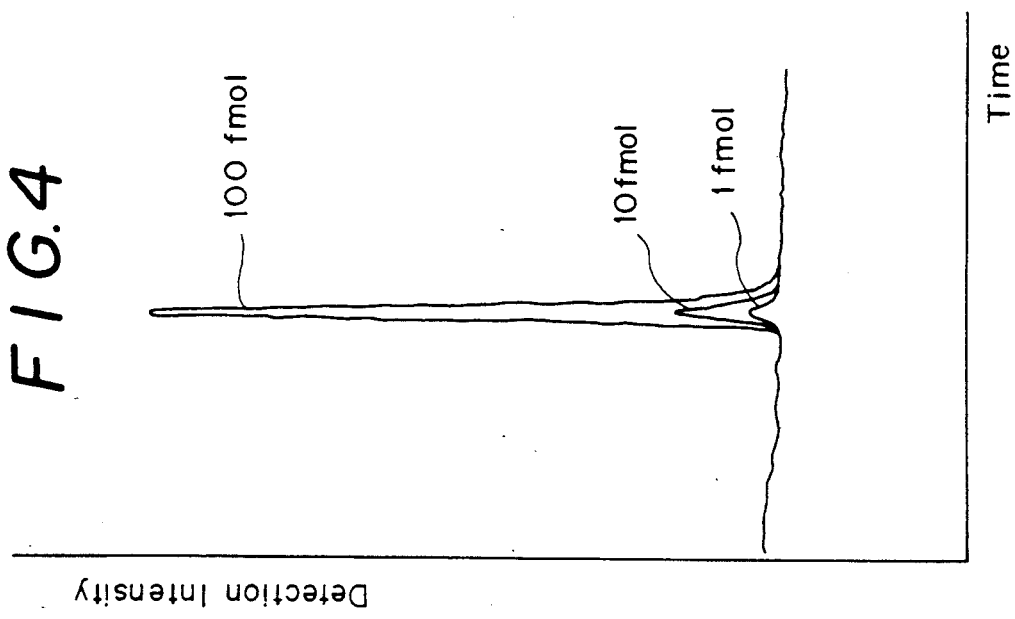
FIG. 3 (i)

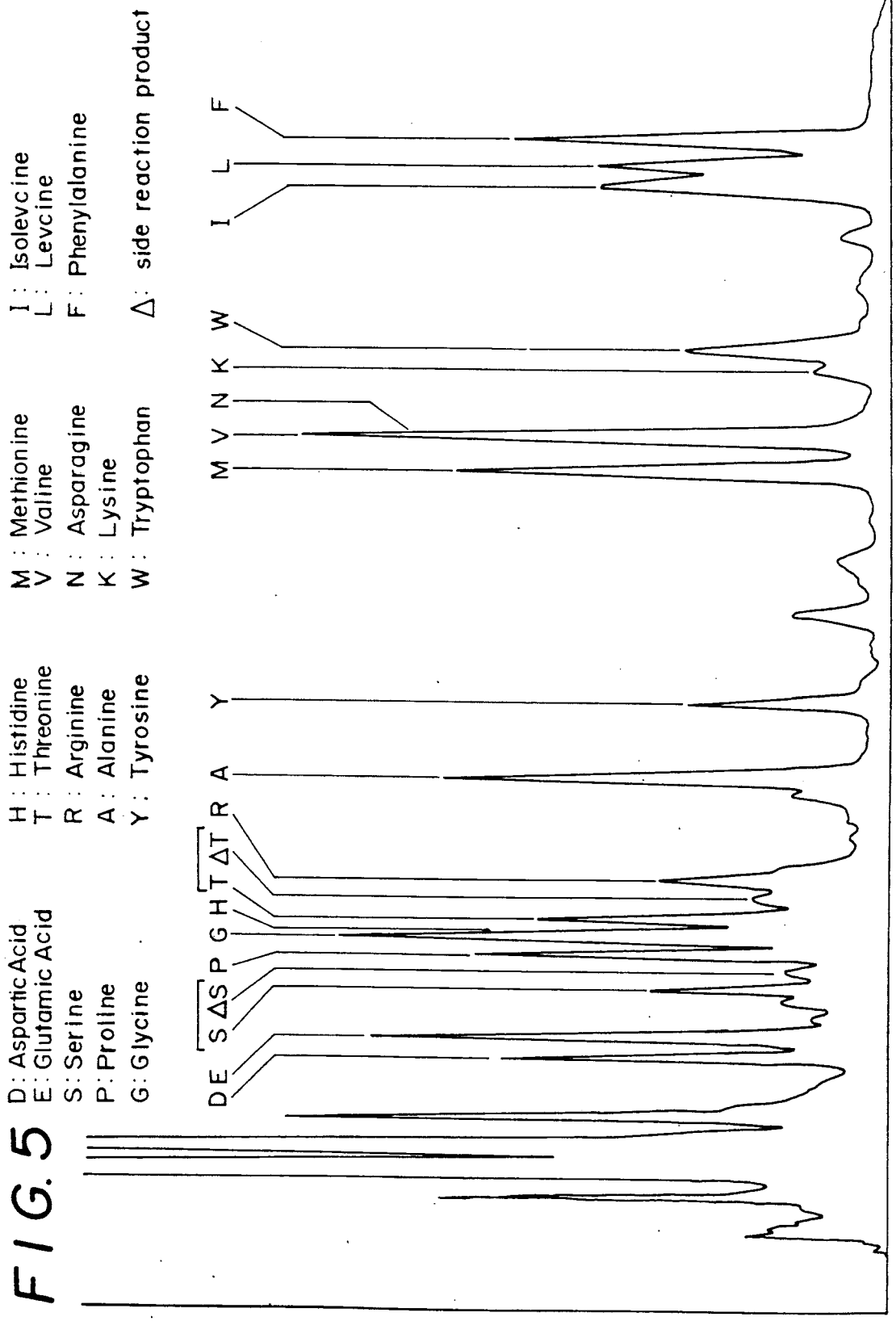

DETECTION METHOD FOR AMINO ACID DERIVATIVE

BACKGROUND OF THE INVENTION

1. Field of the invention

This invention relates to a method for detecting amino acid derivatives for application to sequence determination from the amino(N) terminal of a protein, more particularly to a method for detecting amino acid derivative with high sensitivity by using an amino compound containing a fluorescent amino compound.

2. Description of the prior art

For the detection of amino acids in the final step of the phenylisothiocyanate method according to Edman, P. Acta. Chem. Scand. 10 761 (1956), which is an N-terminal sequence determination method, it has been a usual practice as shown in FIG. 2 that thiazolinone derivatives are treated with an acid to form phenylthiohydantoin (PTH) derivatives and these derivatives are determined spectrophotometrically.

Although the prior art method for spectrophotometrically detecting PTH derivatives is simple and convenient as detection means, it cannot fully cope with a recent trend toward more highly sensitive analysis of a protein with a smaller amount of specimen.

For the high-sensitivity detection of amino acids, methods of using $^{32}$S PITC labelling or $^{135}$I PITC labelling are shown in the following publication, PITC standing for phenylisothiocyanate:

W. G. Lauer, *Fundamental Techniques in Virology*, Eds. K. Habel and N.P. Salgman p. 379 (1961) Academic Press N.Y.

C. J. Burrell, P. D. Cooper, J. M. Swann, Aust J. Chem. 28 2289, (1975).

In the above methods, radioactive isotope derivatives take part in the main reaction in the Edman degradation method. If high radioactivity is used for the purpose of realizing high sensitivity, not only radioactive disintegration increases, which adversely affects a yield itself in the Edman amino acid sequence determination, but also the contamination of the environment occurs.

SUMMARY OF THE INVENTION

Therefore, it is an object of the present invention to provide a novel method for detecting amino acids which can be applied to an amino acid sequence determination from the amino terminal of a protein with higher sensitivity and no contamination of the environment.

This and other objects of the invention are accomplished by a novel method comprising the steps of reacting a 2-anilino-5-thiazolinone derivative of an amino acid with an amino compound of fluorescein or of a rhodamine derivative to form a phenylthiocarbamyl amino acid derivative and detecting the phenylthiocarbamyl amino acid derivative.

BRIEF DESCRIPTION OF THE DRAWINGS

FIG. 1 is a process flowsheet showing the detection method of this invention;

FIG. 2 is a process flowsheet of a prior art method;

FIG. 3(i) is an HPLC chart of an unreacted thiazolinone derivative;

FIG. 3(ii) is an HPLC chart of a reaction product after mixing at room temperature for 3 minutes;

FIG. 4 is an HPLC chart of a phenylthiocarbamyl derivatives of leucine; and

FIG. 5 is an HPLC chart of a mixture of various phenylthiocarbamyl amino acid derivatives.

DETAILED DESCRIPTION OF THE INVENTION

FIG. 1 shows principle flow diagram of the present invention. The method according to the present invention comprises the steps of reacting a 2-anilino-5-thiazolinone derivative with a fluorescent amino compound such as an aminofluorescein or a rhodamine derivative amino compound, to form a PTC amino acid derivative and detecting the amino acid derivative with high sensitivity by making use of a fluorophotometer. In FIG. 1, each of $R_1$, $R_2$ and $R_3$ is an amino acid side chain and X denotes fluorescein or a rhodamine derivative.

The present invention will now be described in more detail with reference to the following examples.

EXAMPLE 1

This example illustrates a basic embodiment of the method according to the present invention in which a 2-anilino-5-thiazolinone derivative of an amino acid (ATZ) is reacted with 4-aminofluorescein to form a phenylthiocarbamyl amino acid derivative and the reaction product is detected with very high sensitivity.

In this Example, a dipeptide (Ala-Gly) is used instead of a protein for simplification.

i) Synthesis and formation of ATZ-Ala (see Molecular Biology, Biochemistry and Biophysics, Vol. 8, "Protein Sequence Determination" edited by Saul B. Neadleman, Springer-Verlag, p. 253)

The reaction proceeds according to the following formulae [IV] and [V]:

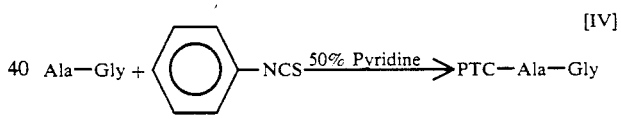

[IV]

Ala-Gly was dissolved in a 50% aqueous pyridine solution, and 2M NaOH was added thereto to adjust the pH value to 8.6. Subsequently, PITC was added thereto. Since the pH value lowered with the addition of PITC, 2M NaOH was added to keep the pH value at 8.6. After the variation in the pH value was hardly observed, the solution was heated at 40° C. for 1 hr. After the completion of the reaction, the reaction mixture was washed with benzene. Benzene dissolved in the water phase was purged with a nitrogen gas, and the pH was adjusted to 2 by the addition of 1M HCl, thereby preparing PTC-Ala Gly in the form of a white precipitate.

[V]

PTC-Ala-Gly thus prepared was dissolved in TFA, and the solution was heated at 50° C. for 5 min. After the completion of the reaction, the reaction mixture was evaporated to dryness. Butyl chloride was added to the residue to thoroughly dissolve the product therein, and the resulting solution was passed through a cellulose column. The by-product and Gly were adsorbed on the column. The effluent was collected and evaporated to dryness, thereby preparing ATZ-Ala in the form of a white crystal.

ii) Coupling reaction

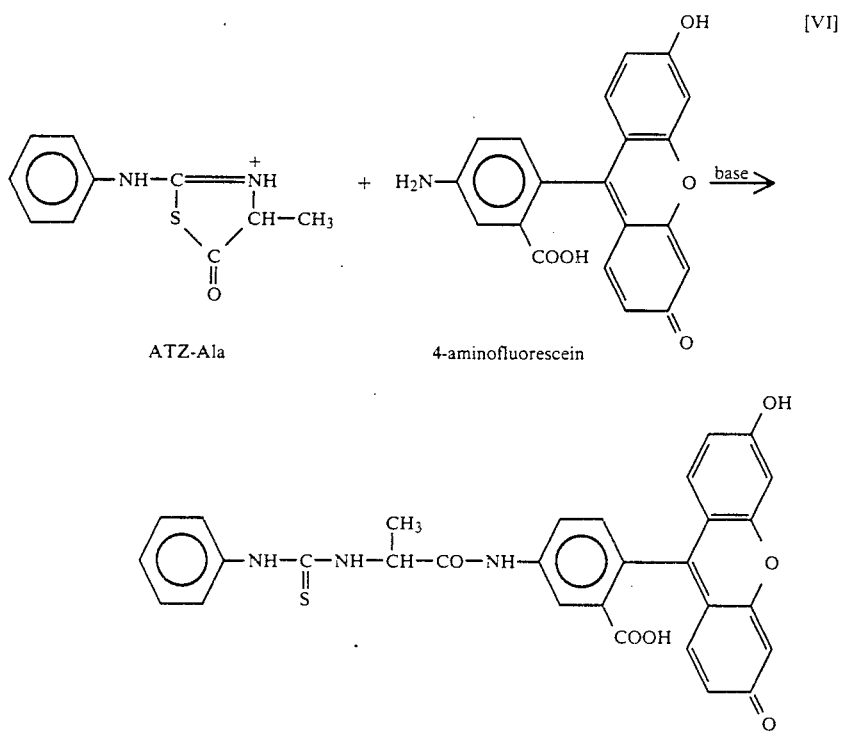

ATZ-Ala     4-aminofluorescein phenylthiocarbamyl amino acid aminoflouroescein
As shown in the above-described reaction formula [VI], the amino group of 4-aminofluorescein attacks the carbonyl group of ATZ amino acid. This reaction is the reverse of a reaction for cleaving a peptide bond between PITC and the peptide. The reaction was conducted at room temperature for 3 min. in a solvent comprising pyridine (10%) and demethylformamide.

iii) Detection of phenylthiocarbamyl amino acid The reaction mixture was applied to high-pressure liquid chromatography (HPLC), and the reaction product was detected with ultraviolet absorption spectra (at 269 nm). The results are shown in FIG. 3.

FIG. 3(i) is an HPLC chromatogram of a thiazolinone derivative, while FIG. 3(ii) is an HPLC chromatogram after the reaction of the thiazolinone derivative for 3 min. In FIGS. 3(i) and 3(ii), (a) is a peak of a thiazolinone derivative of alanine and (b) is a peak of a phenylthiocarbamyl derivative of alanine. As can be seen from the drawings, the coupling reaction between the thiazolinone derivative of alanine and 4-aminofluorescein was completed in 3 min at room temperature, and the thiazolinone derivative was detected in the form of a thiocarbamylalanine derivative.

(Conditions of HPLC)
column:
   SERVA Cat. No. 42318
   250 mm×4.6 mm
   SERVACHROM Packing
solvent system:

| buffer solution | organic solvent |
| --- | --- |
| 0.015M NaOAc + AcOH pH 5 | CH₃CN—MeOH (4:1) |

| buffer solution | organic solvent |
| --- | --- |
| 1 | 5 | effluent flow rate: 1.5 ml/min
detection wave length 269 nm

EXAMPLE 2

This Example shows the results of an experiment wherein a 2-anilino-5-thiazolinone derivative of an amino acid was reacted with 4-aminofluorescein to form a phenylthiocarbamyl amino acid derivative and the maximum sensitivity with which the amino acid derivative can be detected was investigated.

The phenylthiocarbamyl leucine derivative prepared by the same way from a dipeptide (Leu-Gly) was dissolved in methanol, and 1 femto ($10^{-15}$) mol, 10 femto mol and 100 femto mole (10 $\mu$1) thereof were applied to HPLC and detected with a fluorophotometer (an excitation wavelength of 500 nm and a fluorescence wavelength of 516 nm) respectively. The results are shown in FIG. 4.

The comparison of sensitivity of detection according to the present invention with that of the conventional phenylthiohydantoin amino acid detection method (PTH method) gave the following results, i.e., revealed that the sensitivity of detection according to the present invention was much higher than that according to the prior art method.

| detection method | sensitivity of detection |
| --- | --- |
| PTH method | less than 10 pico mol |
| present invention | 1 femto mol |

(Condition of HPLC)
column:

SHISEIDO CAPSEL PAC C18 AG Type
150 mm×4.6 mm
solvent system:
A: 10 mM $Na_2HPO_4$ - $NaH_2PO_4$; pH 8.0
B: MeOH
gradient elution
flow rate: 1 ml/min
temperature: 40° C.
detection:
  excitation wavelength: 486 nm
  fluorescence wavelength: 513 nm

EXAMPLE 3

This Example illustrates an embodiment in which a mixture of phenylthiocarbamyl amino acid derivatives of amino acids constituting a protein was separated into components and detected by HPLC (the condition of HPLC were the same as those of Example 2).

A mixture of phenylthiocarbamyl amino acid derivatives synthesized by making use of dipeptides containing predetermined amino acids according to the procedures described in the Example 1 was analyzed by HPLC under conditions shown in Example 2. The results are shown in FIG. 5. As can be seen from the drawing, the phenylthiocarbamyl derivatives of 20 amino acids which are components constituting a protein were excellently separated.

An important feature of the present invention resides in that a fluorescent amino compound is reacted with thiazolinone derivative of an amino acid to form a phenylthiocarbamyl derivative of the amino compound and the amino acid derivative is detected without using any radioisotope.

In the above Examples, embodiments in which 4-aminofluorescein was used were described. However, it is apparent that other fluorescent amino compounds can be used, and the present invention is not limited to the above Examples only. As is apparent from the foregoing description, the method for detecting an amino acid derivative with high sensitivity is very useful from the viewpoint of industry.

We claim:

1. A method for detecting an amino acid derivative, the method comprising the steps of:
    A. reacting phenylisothiocyanate (d) with a protein or a peptide (e) to form a phenylthiocarbamylprotein or a phenylthiocarbamylpeptide (f);
    B. reacting said phenylthiocarbamylprotein or a phenylthiocarbamylpeptide (f) with an acid in anhydrous condition to effect cyclization and scission and to form a 2-anilino-5-thiazolinone derivative (a);
    c. reacting said 2-anilino-5-thiazolinone derivative (a) with an amino compound of fluorescein or an amino compound of rhodamine derivatives (b) to form a phenylthiocarbamyl amino acid derivative (c) according to the following reaction scheme; and
    D. detecting said phenylthiocarbamyl amino acid derivative (c):

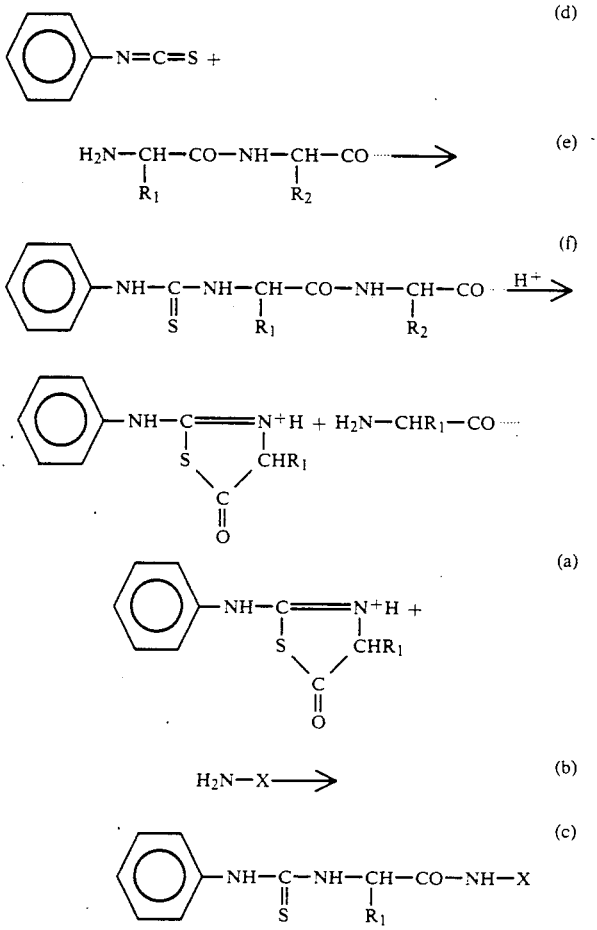

wherein X is a fluorescein or rhodamine derivative and $R_1$ and $R_2$ are amino acid side chains.

* * * * *